(12) United States Patent
Heimdal et al.

(10) Patent No.: US 7,022,078 B2
(45) Date of Patent: Apr. 4, 2006

(54) METHOD AND APPARATUS FOR SPECTRAL STRAIN RATE VISUALIZATION

(75) Inventors: Andreas Heimdal, Olso (NO); Hans Garmann Torp, Trondheim (NO)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 736 days.

(21) Appl. No.: 09/683,893

(22) Filed: Feb. 28, 2002

(65) Prior Publication Data

US 2003/0163044 A1    Aug. 28, 2003

(51) Int. Cl.
*A61B 8/06* (2006.01)

(52) U.S. Cl. .................................................. 600/453

(58) Field of Classification Search ........ 600/437–472; 73/625, 626; 128/916; 367/7, 11, 130, 138
See application file for complete search history.

(56) References Cited

U.S. PATENT DOCUMENTS

| 6,099,471 A | 8/2000 | Torp et al. |
| 6,352,507 B1 | 3/2002 | Torp et al. |
| 6,579,240 B1 * | 6/2003 | Bjaerum et al. ............ 600/447 |

* cited by examiner

*Primary Examiner*—Ali Imam
(74) *Attorney, Agent, or Firm*—McAndrews, Held & Malloy, Ltd.; Peter J. Vogel; Michael A. Dellapenna

(57) ABSTRACT

Methods and apparatus are provided in a diagnostic ultrasound system for generating and displaying strain rate spectrums corresponding to the deformation of a tissue structure within a subject, designated by a sample gate, in response to Doppler signals generated by the ultrasound system. Various combinations of several processing techniques are employed including spectral estimation processing such as discrete Fourier transform (DFT) processing, circular convolution, signal scaling/normalization, and complex autocorrelation.

31 Claims, 8 Drawing Sheets

METHOD AND APPARATUS FOR SPECTRAL STRAIN RATE VISUALIZATION

BACKGROUND OF INVENTION

Certain embodiments of the present invention relate to a diagnostic ultrasound system which measures and images anatomical structures and their movements. More particularly, certain embodiments relate to methods and apparatus for generating and displaying strain rate spectrums associated with moving tissue structure.

Within the field of ultrasound imaging, physicians have become interested in using tissue strain and strain rate for clinical measurements. The term "strain" refers to a characteristic of the tissue being examined. For example, the strain associated with muscle tissue corresponds to a ratio of the muscle tissue's initial length and the change in muscle tissue length during a prescribed time interval. In ultrasound imaging, the rate of change of strain (i.e. strain rate) is typically visually presented to a physician as a colorized 2-dimensional image, where variations in color correspond to different strain rates. It has become apparent that the viability of a segment of the cardiac muscle is related to the amount of muscle strain and temporal behavior of the strain that is performed by, or imposed on the muscle segment. Also, it has been determined that malignant tumors may be detected based on the resistance to compression.

Doppler methods to measure velocities can be divided into two different categories. One method is spectral display and the other is color display. In the spectral method, the Doppler spectrum for a single location in the image is calculated by splitting the ultrasound signal in short-time overlapping windows and calculating the spectrum in each window. The time-varying spectrum is displayed in a frequency-time display with the spectrum magnitude coded as grayscale intensity or color. The color method, on the other hand, calculates the mean Doppler frequency for each point in the image and color encodes it for display. Only the color method has previously been applied to strain rate imaging. In its simplest form, the color represents the difference in mean Doppler frequency at two spatial locations separated by a small distance, divided by the distance. A problem with the color method is that it may be difficult to discern areas in the image that give correct strain rate values and areas that are affected by decorrelation and acoustical noise, since only the mean Doppler frequencies are used.

Reverberations are caused by multiple reflections within the tissue. The reverberations and noise can bias the velocity gradient estimated within the tissue due to correlation with a false or corrupted echo. Falsely increased, decreased or even reversed strain rate estimates may result.

One application of real-time strain rate imaging is in cardiology. The strain rate gives a direct and quantitative measure for the ability of the myocardium to contract and relax. By imaging along the myocardium from an apical view, the local strain rate component along the long axis of the heart can be measured. Measuring the local strain rate component gives information about the local shortening and lengthening of the heart wall. By imaging from the parasternal view, the strain rate component perpendicular to the heart wall gives information about the local thickening of the muscle. Wall thickening measured with M-mode or from the 2D image is a commonly used measure for muscle viability. With strain rate imaging, a direct measure for this thickening is available. The strain rate images can potentially add to the diagnosis of a number of cardiac disorders.

To understand strain rate in more detail, it is assumed that a segment of tissue of initial length $L_O$ may be stretched or compressed or lengthens or contracts to a different length L. The one-dimensional strain, defined as $$\varepsilon = \frac{L - L_o}{L_o} \tag{1}$$

represents a dimensionless description of the change. If the length L is considered to be a function of time, L(t), the temporal derivative of the strain, the strain rate, can be found using the equation $$\dot{\varepsilon} = \frac{\delta \varepsilon}{\delta t} \tag{2}$$

If the velocity, v of every point in the object is known, an equivalent definition of the strain rate is $$\dot{\varepsilon} = \frac{\delta v}{\delta r} \tag{3}$$

The equations also provide a useful description of the deformation of the tissue segment. The strain rate measures the rate of the deformation of the segment. If the strain rate is zero, the shape of the segment is not changing. If the strain rate is positive, the length of the segment is increasing, and if the strain rate is negative, the length of the segment is decreasing.

U.S. Pat. No. 6,099,471 to Torp et al. is directed to a method and apparatus for real-time calculation and display of strain in ultrasound imaging. Ser. No. 09/432,061 to Torp et al. is directed to a method and apparatus for providing real-time calculation and display of tissue deformation in ultrasound imaging.

A need exists for an approach to easily visualize strain rates such that an improved indication of the quality of the strain rate estimates due to the presence or absence of reverberation and other sources of noise may be directly assessed and such that more overall strain rate detail is shown for a particular tissue location.

SUMMARY OF INVENTION

Embodiments of the present invention provide an ultrasound system for generating and displaying strain rate spectrums corresponding to moving tissue structure within a subject, designated by a sample gate, in response to complex Doppler signals generated by the ultrasound system. Various combinations of several processing techniques are employed including spectral estimation processing such as discrete Fourier transform (DFT) processing, circular convolution, signal scaling/normalization, and complex autocorrelation.

Apparatus is provided for generating and displaying strain rate spectrums of moving tissue structure within a subject, designated by a sample gate, in response to complex Doppler signals generated by an ultrasound system. The apparatus includes a Doppler processor and a strain rate processor for performing various combinations of several functions that include spectral estimation processing such as discrete Fourier transform (DFT) processing, circular convolution, signal scaling/normalization, and complex autocorrelation.

A method is also provided for generating and displaying strain rate spectrums of moving tissue structure within a subject, designated by a sample gate, in response to complex Doppler signals generated by an ultrasound system. The method includes performing combinations of various processing functions including spectral estimation processing such as discrete Fourier transform (DFT) processing, circular convolution, signal scaling/normalization, and complex autocorrelation.

Certain embodiments of the present invention afford an approach to generating and displaying strain rate spectrums to easily visualize strain rates for a particular tissue segment within a subject such that an improved indication of the quality of the strain rate estimates due to the presence or absence of reverberation and other sources of noise may be directly assessed and such that more overall strain rate detail is shown.

DETAILED DESCRIPTION

Figure 1:
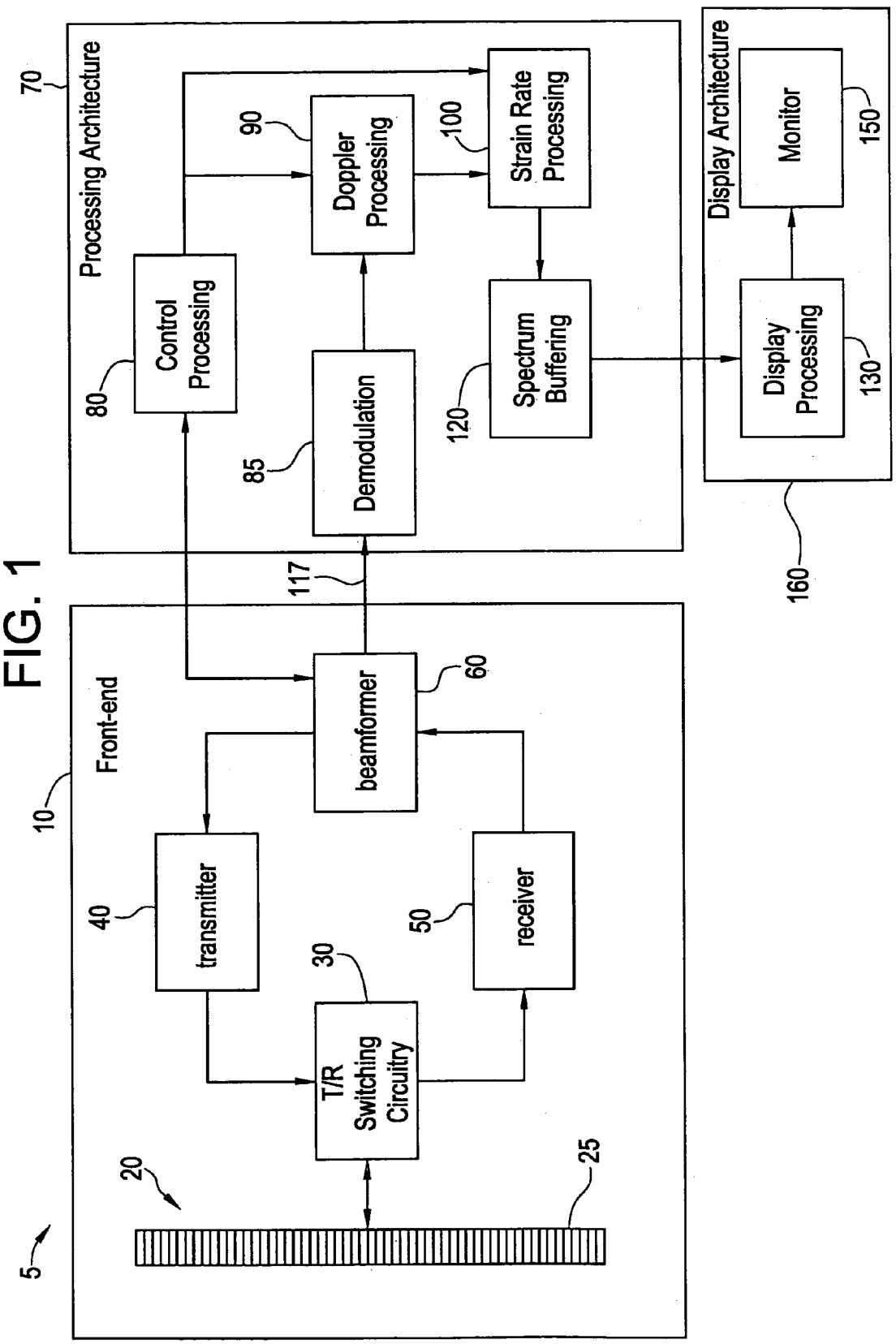
FIG. 1 is a schematic block diagram of an ultrasound system illustrating strain rate processing in relation to other elements of the system in accordance with an embodiment of the present invention.

FIG. 1 is a schematic block diagram of the ultrasound system 5 showing the architecture used to create spectral strain rate images in accordance with one embodiment of the present invention. The illustrated elements of the ultrasound system are the front-end 10, the processing architecture 70, and the display architecture 160. Front-end 10 comprises a transducer array 20 (comprising a plurality of transducer elements 25), transmit/receive switching circuitry 30, a transmitter 40, a receiver 50, and a beamformer 60. Processing architecture 70 comprises a control processing module 80, a demodulation module 85, a Doppler processing module 90, a strain rate processing module 100, and a spectrum buffer module 120. Display architecture 160 comprises display processing module 130 and a monitor 150.

In the front-end 10, the transducer array 20 is connected to the transmit/receive (T/R) switching circuitry 30. The T/R switching circuitry 30 is connected to the output of transmitter 40 and the input of receiver 50. The output of receiver 50 is connected to beamformer 60. Beamformer 60 is further connected to the input of transmitter 40, an input of control processing module 80, and the input of demodulation module 85 in processing architecture 70.

Figure 1B:
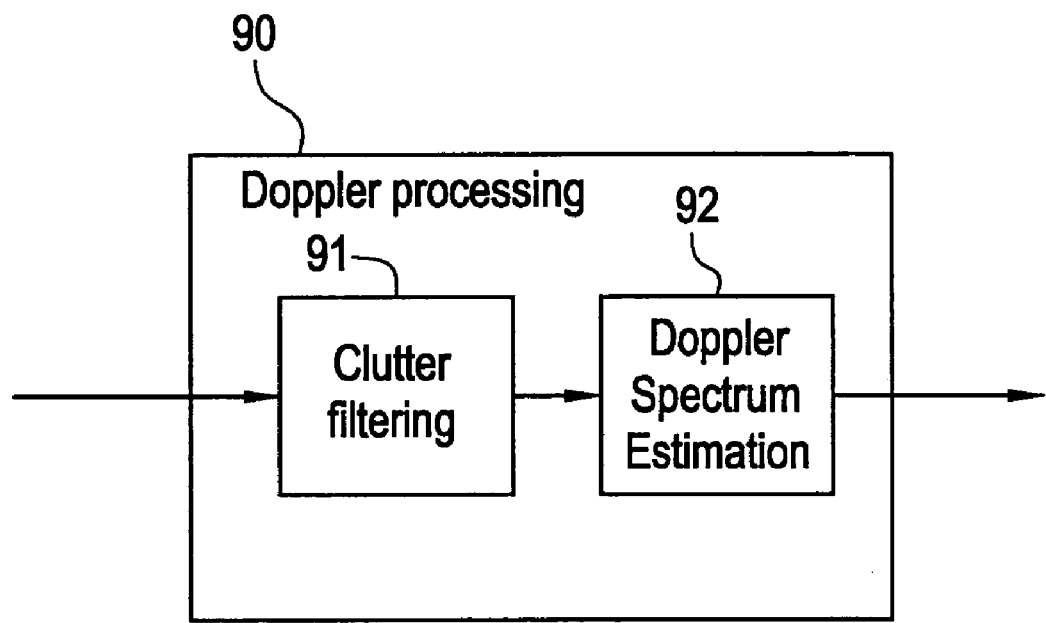
FIG. 1B illustrates a Doppler processing module of the ultrasound system of FIG. 1 in accordance with an embodiment of the present invention.

In processing architecture 70, control processing module 80 is connected to Doppler processing module 90 and strain rate processing module 100. The output of demodulation module 85 is connected to an input of Doppler processing module 90. The output of Doppler processing module 90 is connected to an input of strain rate processing module 100. The output of strain rate processing module 100 is connected to the input of spectrum buffer module 120. The output of spectrum buffer module 120 is connected to the input of display processing module 130 in display architecture 160. In display architecture 160, the output of display processing module 130 is connected to monitor 150. Doppler processing module 90 includes a clutter filter 91 and a Doppler spectrum estimator 92 as shown in FIG. 1B.

When data is to be sampled from a subject, the transducer array 20 is used to transmit ultrasound waves into the subject. The transducer array 20 may be a linear array or a curved array of many individual transducer elements 25. Each transducer element 25 is capable of generating ultrasound waves in response to a signal from the transmitter 40. In addition, the phase relationship of the ultrasound waves between transducer elements may be controlled. The result is an ultrasound beam of energy being transmitted into a subject at a certain angle with respect to an orthogonal direction to the surface of the transducer array 20 and effectively originating from a point on the surface of the transducer array 20. Multiple elements 25 are typically used to transmit an ultrasound beam. The phase relationship between the ultrasound waves transmitted from the multiple elements 25 determines the steering angle of the beam being transmitted. The number of transducer elements 25 used for transmission, as well as other factors such as apodization, determine the shape of an ultrasound beam along its length within a subject.

Figure 2:
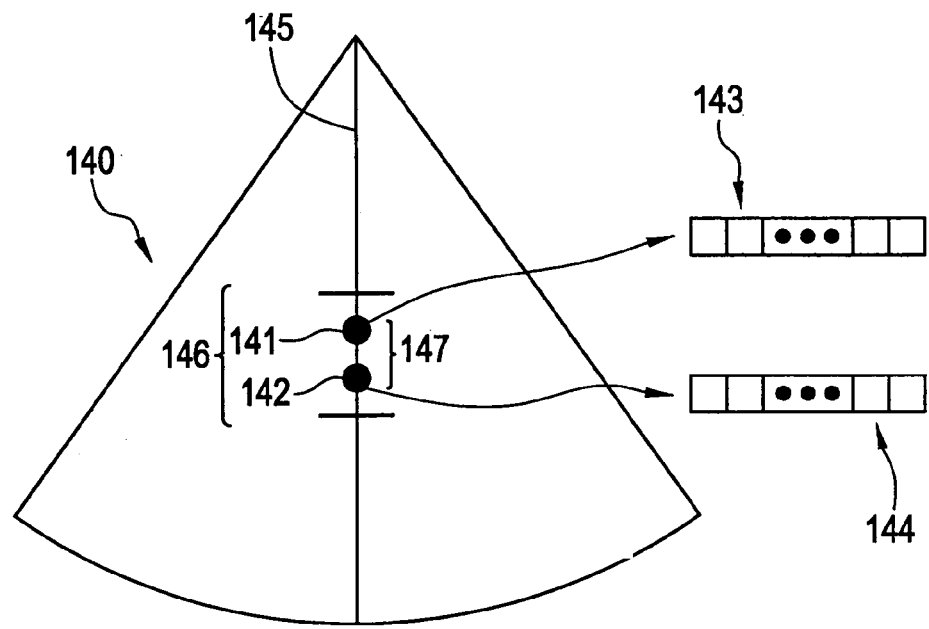
FIG. 2 illustrates a scan plane with two sample volume locations bounding a tissue segment within a sample gate positioned by a user of the system of FIG. 1 in accordance with an embodiment of the present invention.

To generate a transmitted ultrasound beam, the control processing module 80 sends command data to the beamformer 60 which tells the beamformer to generate transmit parameters to create a beam of a certain shape that originates from a certain point at the surface of the transducer array 20 at a certain steering angle within a scan plane 140 (see FIG. 2) along a scan line (e.g. 145). The transmit parameters are sent from the beamformer 60 to the transmitter 40. The transmitter 40 uses the transmit parameters to properly encode transmit signals to be sent to the transducer array 20 through the T/R switching circuitry 30. The transmit signals are of certain levels and phases with respect to each other and are provided to individual transducer elements 25 of the transducer array 20. The transmit signals excite the transducer elements 25 of the transducer array 20 to emit ultrasound waves with the same phase and level relationships as that of the transmit signals. As a result, a transmitted beam of ultrasound energy is formed within the tissue of a subject within a scan plane 140 along a scan line (e.g. 145) when the transducer array 20 is acoustically coupled to the subject by using, for example, ultrasound gel. The process is known as electronic scanning. For Doppler applications, the transmit signals are typically transmitted as multiple pulses at a pulse repetition frequency (PRF). Reflections of the multiple pulses are used to make up a complex Doppler signal on receive. The Doppler signal is typically split in short-time overlapping data packets for further processing. A tissue segment to process along a scan line (e.g. 145) is typically designated by a sample gate 146 that is positioned within the scan plane 140 by the ultrasound operator.

The transducer array 20 is a two-way transducer. Once ultrasound waves are transmitted into a subject, these waves are backscattered off of sample volumes of tissue within the structure of the subject. The backscattered waves arrive at the transducer array 20 at different times, depending on the distance into the tissue they returned from and the angle with respect to the surface of the transducer array 20 at which they return. The transducer elements 25 of the transducer array 20 are responsive to the backscattered waves and convert the ultrasound energy from the backscattered waves into received electrical signals.

The received electrical signals are routed through the T/R switching circuitry 30 to the receiver 50. The receiver 50 amplifies and digitizes the received signals and provides other functions such as gain compensation. The digitized received signals correspond to the backscattered waves received by each transducer element 25 at various times and preserve the amplitude and phase information of the backscattered waves.

The digitized received signals are sent to beamformer 60. The control processing module 80 sends command data to beamformer 60. Beamformer 60 uses this command data to form a receive beam originating from a point on the surface of the transducer array 20 at a steering angle typically corresponding to the point and steering angle of the previously transmitted ultrasound beam. The beamformer 60 operates on the appropriate received signals by performing time delaying and focusing, according to the instructions of the command data from the control processing module 80, to create received beam signals corresponding to sample volumes along a scan line (e.g. 145) in the tissue structure of the subject. The phase, amplitude, and timing information of the received signals from the various transducer elements 25 are used to create the received beam signals.

The received beam signals are sent to processing architecture 70 over digital interface 17. Demodulation module 85 performs demodulation on the received beam signals to create pairs of I and Q demodulated data values corresponding to sample volumes (e.g. 141 and 142) along the length of a scan line (e.g. 145) within the sample gate 146 corresponding to the received beam. Demodulation is accomplished by comparing the phase and amplitude of the received beam signals to a reference frequency. The I and Q demodulated data values preserve the phase and amplitude information of the received signals. The amplitude information of an I and Q data pair for a given sample volume location is mathematically equivalent to $$\sqrt{I^2+Q^2}$$

The phase information is mathematically equivalent to $$\tan^{-1}\left(\frac{Q}{I}\right)$$

Thus, a single amplitude data value and a single phase data value may be yielded for a single I and Q data pair corresponding to a sample volume location. The data values are also referred to as complex Doppler data, since any shift in phase due to the Doppler effect is inherent in the data. The demodulated I and Q data pairs corresponding to the received beam are sent to Doppler processing module 90 in the form of Doppler data packets (e.g. 143 and 144) where they are subsequently processed to ultimately be displayed in a strain rate spectrogram image. A complex Doppler data packet comprises multiple I and Q data pairs sampled from a sample volume location at a certain rate known as the PRF. Subsequent packets may consist of partly the same data, since an overlapping technique may be used when building up the data packet. A typical Doppler packet may include, for example, 128 complex I and Q data pairs. The Doppler processing module 90 may or may not include a clutter filter to remove low velocity components in the Doppler packet prior to further processing. It may also include a Doppler Spectrum Estimator.

Reverberations are caused by multiple reflections within the tissue. The reverberations and noise can bias the velocity gradient that is estimated within the tissue due to correlation with a false or corrupted echo. The result may be falsely increased, decreased or even reversed strain rate estimates.

In an embodiment of the present invention, the strain rate spectrogram for a tissue segment designated by a sample gate 146 within a scan plane 140 is generated and displayed in a strain rate versus time format (or, alternatively, a Doppler frequency difference versus time format). The entire strain rate spectrogram 200 is generated and displayed for a given tissue segment over time (see FIG. 3). Each column in the strain rate spectrogram 200 represents a strain rate spectrum 201 (see FIG. 4) at a given time instance. The magnitude 202 in the strain rate spectrum is mapped as intensity or color in the strain rate spectrogram image. In addition to showing the mean strain rate, the spectrums and spectrogram provide an indication of the quality of the strain rate estimates for the tissue segment. A narrow bandwidth in the spectrogram may indicate a signal of good quality, while a broad bandwidth may indicate a noisy signal. Also, a gap or absence of a clear peak in the spectrogram may be an indication of noise in the signal. The coordinate system of FIG. 4 is represented by a time axis 190, a strain rate axis 170, and a Doppler frequency difference axis 180. The coordinate system of FIG. 4 is represented by a Doppler frequency difference axis 180 and a spectrum magnitude axis 202.

Figure 5:
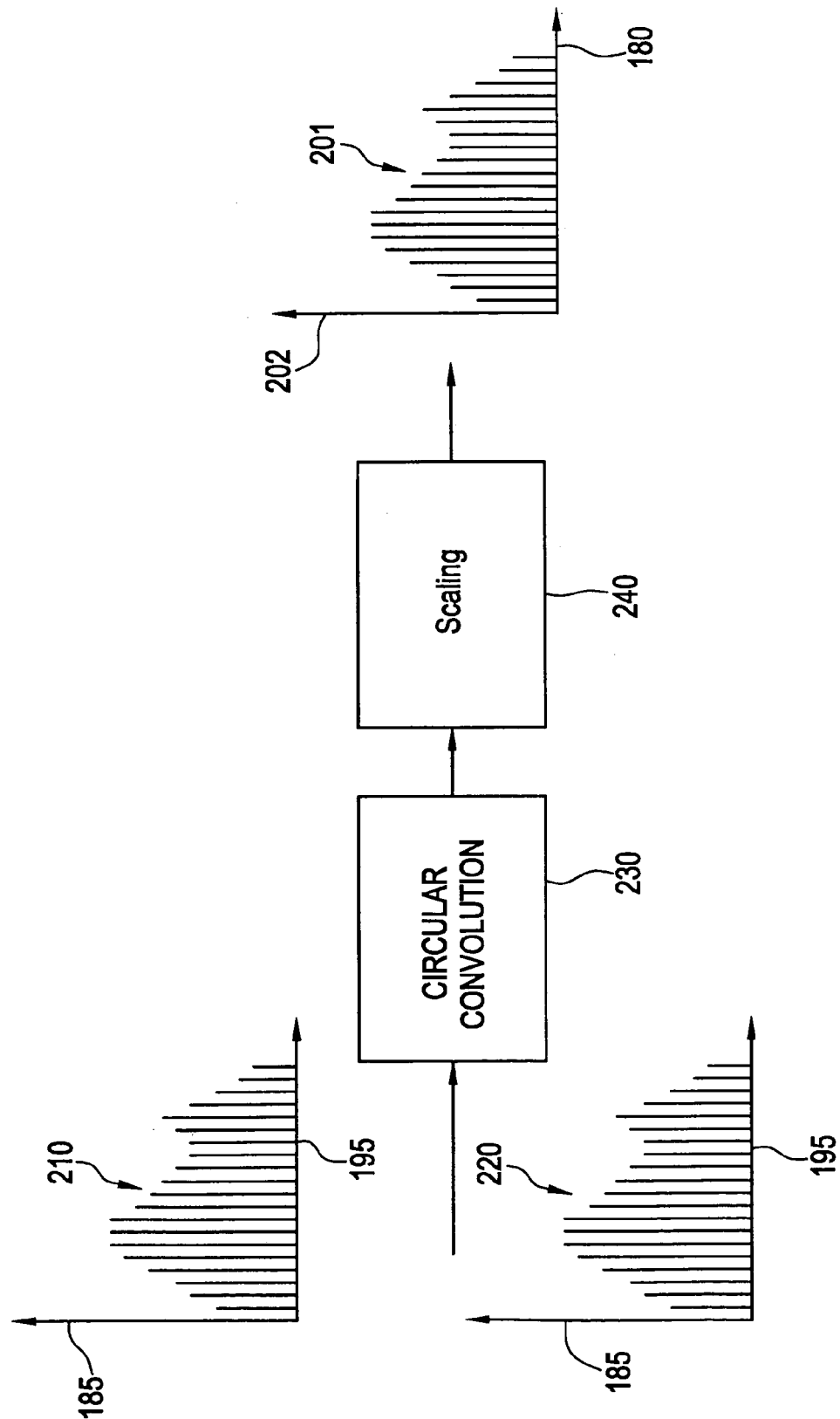
FIG. 5 illustrates spectral strain rate processing in accordance with a first embodiment of the present invention.

FIG. 5 illustrates one embodiment of performing strain rate spectral visualization using strain rate processor 100. Doppler spectrums 210 and 220 are computed by Doppler processor 90 for two sample volume locations 141 and 142 that are separated by a distance dr 147 (see FIG. 2). The Doppler spectrums 210 and 220 may be represented in either real or complex form, i.e., either magnitude only or both magnitude and phase. In FIG. 5 the Doppler spectrums are illustrated as magnitude 185 versus Doppler frequency 195. Each Doppler spectrum is calculated, for example, in the well-known manner of performing a DFT or another spectrum estimator 92 on a packet of complex pairs of Doppler I and Q samples. A clutter filter 91 may be employed to reduce low velocity components in the Doppler packets, but is optional. The Doppler spectrums 210 and 220 are sent to strain rate processor 100 representing magnitude (and possibly phase) versus Doppler frequency. In step 230 of FIG. 5, the strain rate spectrum $P_{sr}(k)$ 201 (unscaled) is calculated from the two Doppler spectrums $P_1(k)$ 210 and $P_2(k)$ 220 as $$P_{SR}(k)=P_1(-k)\circledast P_2(k) \qquad [4]$$

where k is a frequency index corresponding to the frequency separation between adjacent spectral lines along the frequency difference axis 180 and $\circledast$ is the circular convolution operator. A single strain rate spectrum is generated for each time index across the spectrogram image.

The strain rate spectrum is then scaled in magnitude for better visualization in step 240. The scaling may be a simple normalization such as $$X_{SR}(k) = \frac{P_{SR}(k)}{\sum_{l} P_{SR}(l)} \quad [5]$$

where $X_{SR}(k)$ is the normalized strain rate spectrum and/is a subset of the indices k across the frequency difference axis 180.

The spectrum buffer module 120 is programmed to take the scaled strain rate spectrums $X_{SR}(k)$, from consecutive time instances and combine them in a frequency difference versus time format, i.e., a spectrogram. To improve the quality, the spectrum buffer module 120 may also average several scaled strain rate spectrums corresponding to different sample gates 146 prior to including them in the spectrogram. The spectrum buffered data is then sent to display architecture 160 to be processed by display processing module 130 where any final spatial or temporal averaging of the data is performed and grayscale or color is applied to the data. Finally, the resultant data is displayed on monitor 150 to the operator as a 2D spectrogram image where variations in grayscale (or color) correspond to different strain rate magnitude values within the spectrums.

Figure 3:
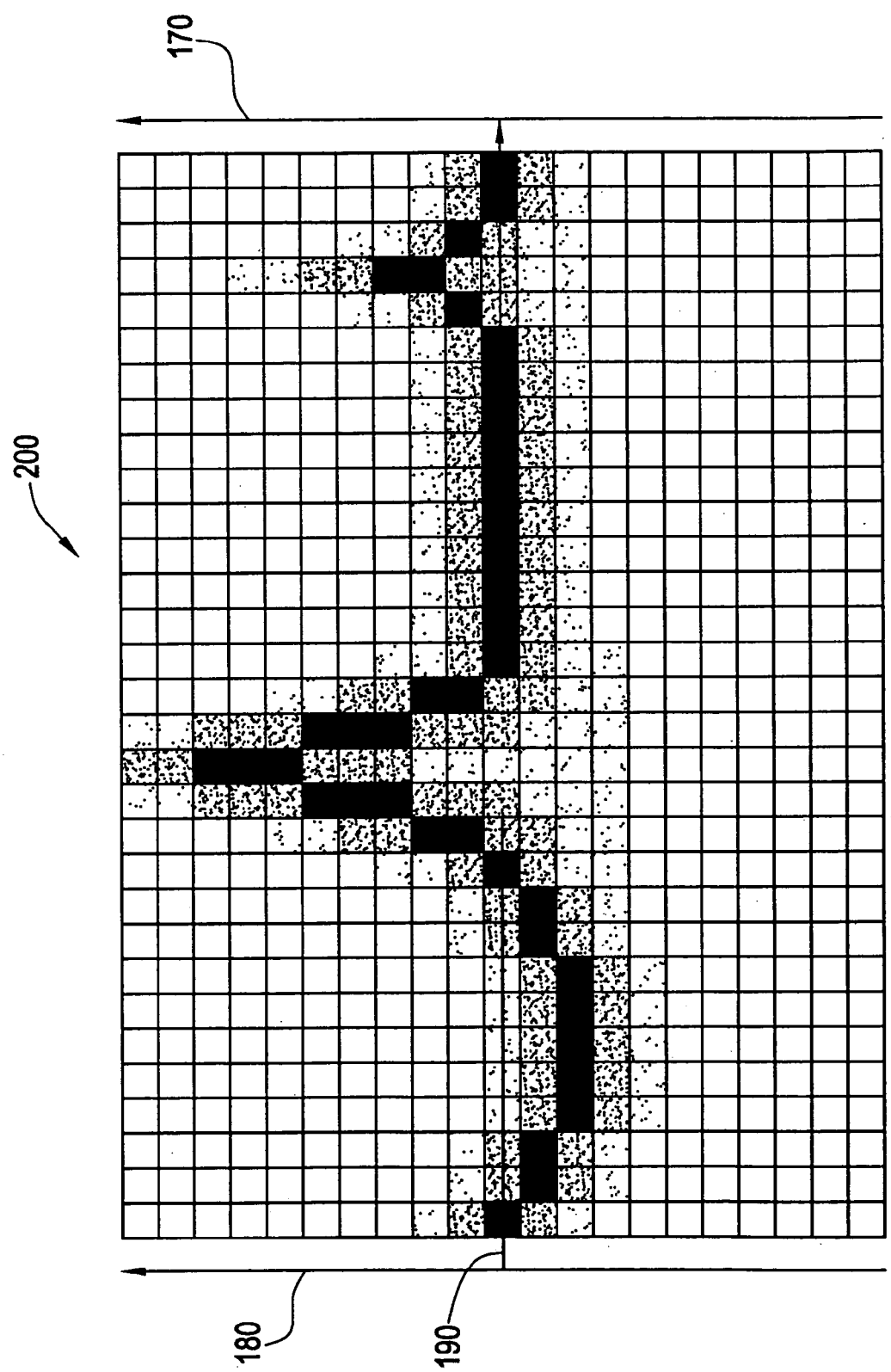
FIG. 3 is an exemplary illustration of a strain rate spectrogram image comprising a plurality of strain rate spectrums generated in accordance with an embodiment of the present invention.
Figure 4:
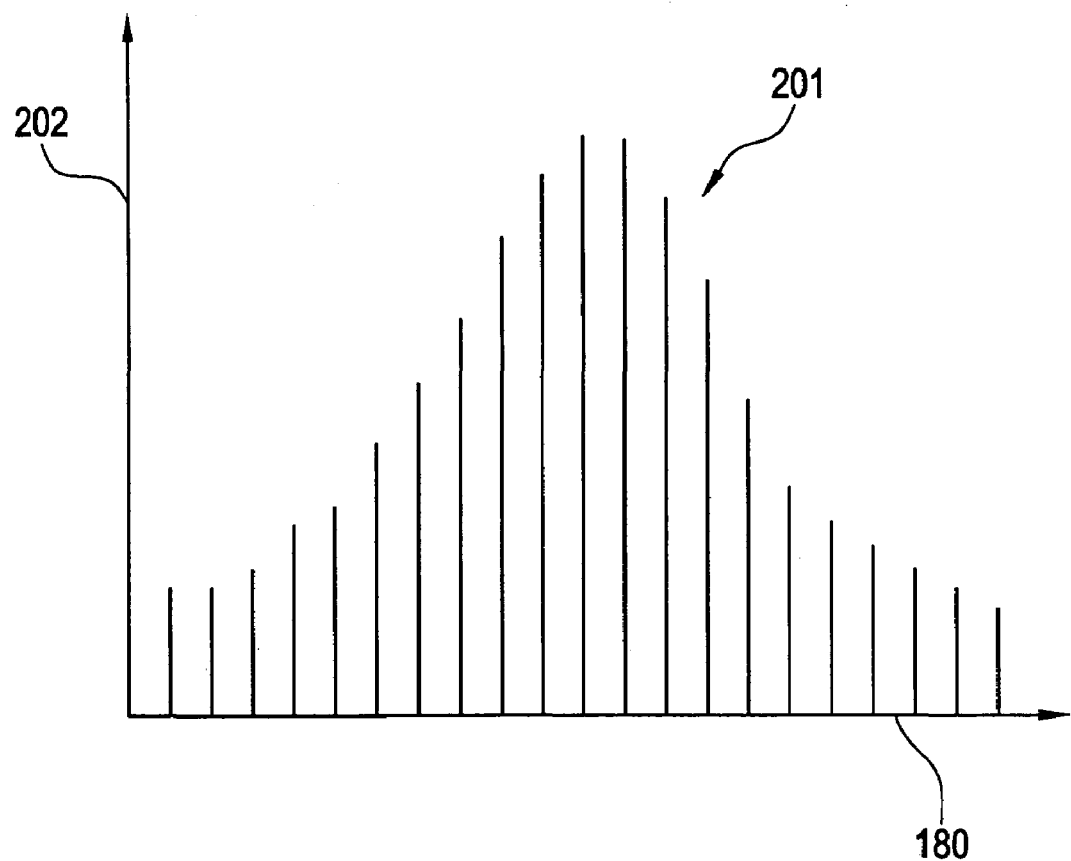
FIG. 4 illustrates a single strain rate spectrum generated in accordance with an embodiment of the present invention.

FIG. 3 is an exemplary illustration of how the strain rate spectrogram image may be displayed. The horizontal display axis is the time axis 190 in, for example, units of seconds and the vertical display axis may be a strain rate axis 170 in units of seconds$^{-1}$ or, alternatively, a Doppler frequency difference axis 180 in units of Hertz. The proper scaling of the vertical display axis for display in a particular set of units is accomplished by accounting for such parameters as the distance between the sample volume locations dr 147, the PRF, the speed of sound in the tissue c, and the ultrasound frequency of transmission $f_0$. The scaling of the vertical display axis may be easily accomplished by one skilled in the art.

Figure 6:
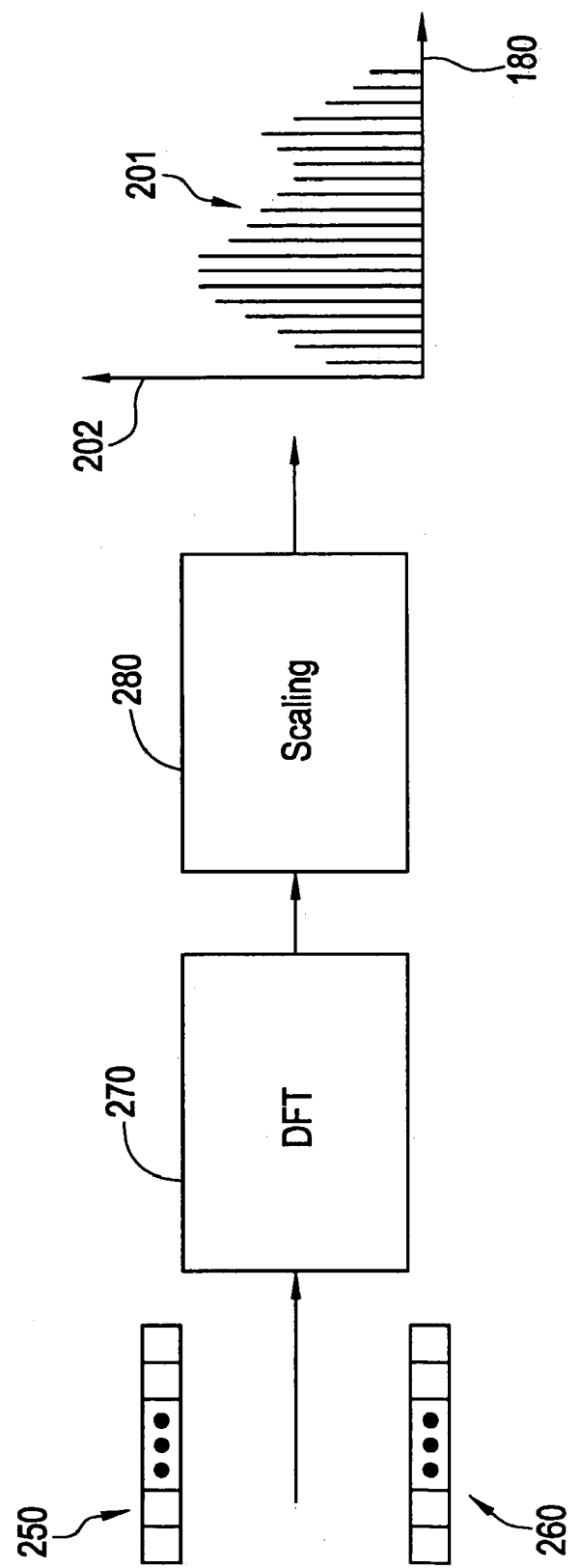
FIG. 6 illustrates spectral strain rate processing in accordance with a second embodiment of the present invention.

In a second embodiment, each strain rate spectrum $P_{SR}(k)$ 201 in the strain rate spectrogram 200 for a tissue segment may be estimated by the strain rate processor 100 from two complex Doppler I and Q packets (e.g. 250 and 260) as shown in FIG. 6. The packets correspond to two sample volume locations 141 and 142 within the scan plane 140 for a certain time window. Clutter filtering of the packets may be performed prior to further processing. A DFT (or any other spectrum estimator) is performed on the complex Doppler packets 250 and 260 as $$P_{SR}(k) = DFT[x(d_1)^* \, x(d_2)] \quad [6]$$

where $x(d_1)$ 250 and $x(d_2)$ 260 are the complex Doppler packets comprising complex pairs of Doppler I and Q samples corresponding to depths $d_1$ 141, and $d_2$ 142, ($d_1$+dr) for a given time window. The complex Doppler packets are passed from demodulation module 85 to strain rate processing module 100 through Doppler processing module 90, where clutter filtering may take place. DFT is the discrete Fourier transform operation and * indicates the complex conjugate operation. A strain rate spectrum is computed in this manner for each time index in the spectrogram 200. The spectrum is then scaled or normalized for display in step 280. Again, proper scaling of the vertical display axis for display in a particular set of units is accomplished.

Figure 7:
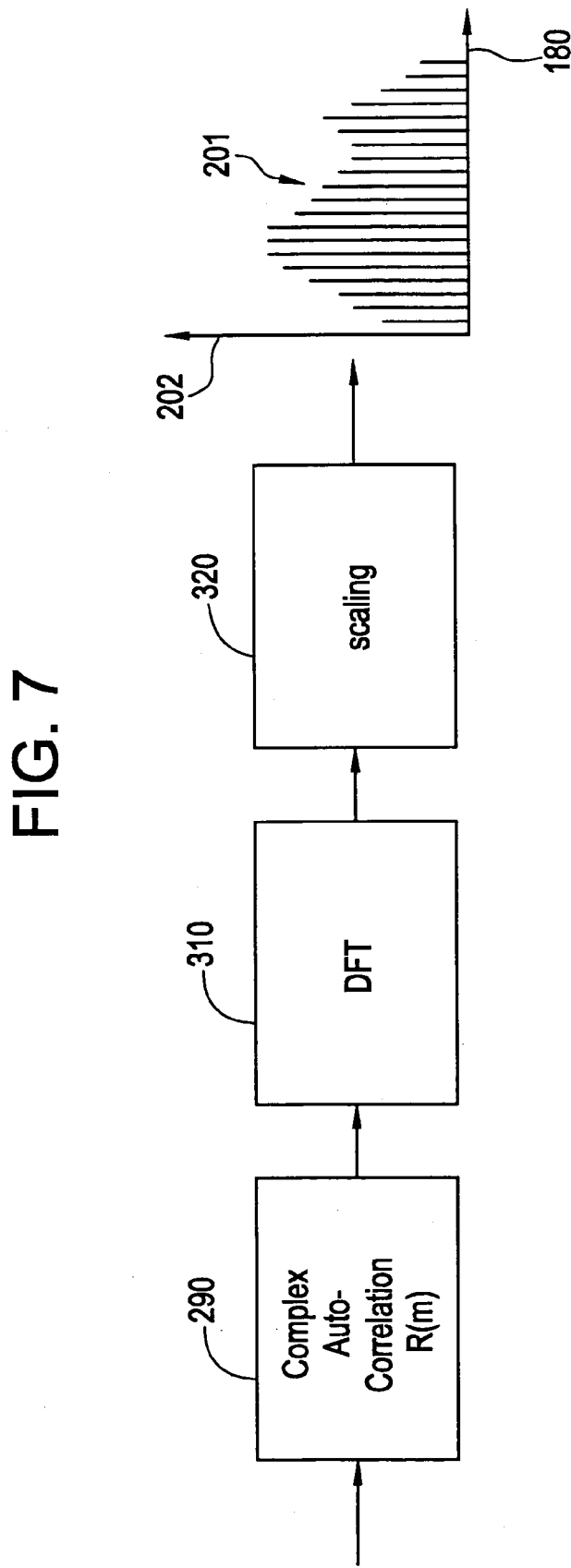
FIG. 7 illustrates spectral strain rate processing in accordance with a third embodiment of the present invention.

The previous two embodiments of spectral strain rate visualization rely only on samples from two sample volume locations (e.g. 141 and 142) within the scan plane separated by a small distance dr 147. However, in a third embodiment, an extension may be made to use more than two sample volume locations from M depths within a tissue segment along the scan line 145 within the sample gate 146. FIG. 7 illustrates that the strain rate processor 100 performs processing in three steps in the third embodiment.

In step 290 of FIG. 7, the strain rate processor 100 computes a complex autocorrelation packet R(m) consisting of a set of complex autocorrelation values for each depth index m from M complex Doppler I and Q packets of length N for a given time index. The calculation may be performed as $$R(m) = \sum_{n=0}^{N-1} x(m,n)^* x(m, n+1) \quad [7]$$

where x(m,n) is the complex Doppler I and Q packet at depth m, with packet sample index n, and * represents the complex conjugate operation.

The complex autocorrelation packet R(m) is processed in step 310 to generate the values of a strain rate spectrum 201 for a particular time index in the strain rate spectrogram 200. A DFT (or any other spectrum estimator) is performed on the M depth samples of R(m) in step 310 as $$P_{SR}(k) = DFT[R(m)] \quad [8]$$

to generate a strain rate spectrum 201 for a particular time index. The spectrum may typically comprise M spectral samples as a result of the DFT. Note that the DFT in this embodiment is performed in the spatial direction and not in the temporal direction as in the two previous embodiments. The process is repeated to generate each spectrum in the strain rate spectrogram 200.

The third embodiment requires more processing than the first two embodiments described above but may also yield a more accurate estimate of the strain rate spectrum over the tissue segment. Again, the spectrum is then scaled or normalized in step 320 for display and the vertical display axis is scaled according to the desired units to be displayed.

Again, for any of the embodiments, spectrum buffer module 120 is programmed to take the spectral strain rate data from consecutive time instances and combine them in a frequency difference versus time format, i.e., a spectrogram. To improve the quality, the spectrum buffer module 120 may also average several scaled strain rate spectrums corresponding to different sample gates 146 prior to including them in the spectrogram. The spectrum buffered data is then sent to display architecture 160 to be processed by display processing module 130 and displayed on monitor 150 to the operator as a 2D spectral image where variations in grayscale (or color) correspond to different strain rate spectrum magnitude values.

The processing for any embodiment of the present invention may performed by dedicated hardware elements such as circuit boards with digital signal processors or may be software running on a general purpose computer or processor such as a commercial, off-the-shelf PC. The various processing modules may be combined or separated according to various embodiments of the present invention. For example, the Doppler processing module 90 and strain rate processing module 100 may be combined into a single processing element.

The processing described above may be done in real-time as an integral feature of the ultrasound system 5. Alternatively, complex Doppler I and Q data or Doppler spectral data may be stored and processed by the ultrasound system such that strain rate processing is performed as a post processing feature, independent of real-time scanning. As a further alternative, complex Doppler I and Q data or Doppler spectral data may be captured from the ultrasound system 5 and the strain rate processing and subsequent display may be performed as a post processing feature outside of the ultrasound system 5, such as on an external PC.

The clutter filter 91 is not compulsory and it is possible to circumvent the clutter filter 91. It is also possible to circumvent the Doppler spectrum estimator 92 for certain possible embodiments. The clutter filter 91 is possible to use even if the Doppler spectrum estimator 92 is not used.

In summary, the advantages and features include, among others, the ability to easily visualize strain rates in a spectral format such that an improved indication of the quality of the strain rate estimates, due to the presence or absence of reverberation and other sources of noise, may be directly assessed and such that more overall strain rate detail is shown for a particular tissue segment.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. Apparatus for generating and displaying a plurality of strain rate spectrums in response to Doppler data generated by an ultrasound system, said apparatus comprising a strain rate processor being responsive to said Doppler data to generate said plurality of strain rate spectrums, wherein said strain rate processor comprises:
   a first element being responsive to said Doppler data to generate a plurality of raw strain rate spectrums; and
   a second element being responsive to said plurality of raw strain rate spectrums to generate said plurality of strain rate spectrums.

2. The apparatus of claim 1 wherein said first element comprises a circular convolution element being responsive to said Doppler data to generate said plurality of raw strain rate spectrums, said Doppler data comprising two sets of Doppler spectrums; and wherein said second element comprises a scaling element being responsive to said plurality of raw strain rate spectrums to generate said plurality of strain rate spectrums, said plurality of strain rate spectrums comprising scaled magnitude values.

3. The apparatus of claim 2 wherein said two sets of Doppler spectrums comprise a first set of Doppler spectrums corresponding to a first sampled depth along an ultrasound beam generated by said ultrasound system and a second set of Doppler spectrums corresponding to a second sampled depth along said ultrasound beam.

4. The apparatus of claim 1 wherein said first element comprises a spectral estimating element being responsive to said Doppler data to generate said plurality of raw strain rate spectrums, said Doppler data comprising two sets of complex Doppler packets; and wherein said second element comprises a scaling element being responsive to said plurality of raw strain rate spectrums to generate said plurality of strain rate spectrums, said plurality of strain rate spectrums comprising scaled magnitude values.

5. The apparatus of claim 4 wherein said two sets of complex Doppler packets comprise a first set of complex Doppler packets corresponding to a first sampled depth along an ultrasound beam generated by said ultrasound system and a second set of complex Doppler packets corresponding to a second sampled depth along said ultrasound beam.

6. The apparatus of claim 5 wherein said spectral estimating element is responsive to the complex conjugate of a first complex Doppler packet from said first set of complex Doppler packets and a second complex Doppler packet from said second set of complex Doppler packets to generate a single raw strain rate spectrum of said plurality of raw strain rate spectrums.

7. The apparatus of claim 1 wherein said strain rate processor comprises: a complex autocorrelation element being responsive to said Doppler data to generate a plurality of complex autocorrelation packets, said Doppler data comprising a plurality of complex Doppler packets; wherein said first element comprises a spectral estimating element being responsive to said plurality of complex autocorrelation packets to generate said plurality of raw strain rate spectrums; and wherein said second element comprises a scaling element being responsive to said plurality of raw strain rate spectrums to generate said plurality of strain rate spectrums, said plurality of strain rate spectrums comprising scaled magnitude values.

8. The apparatus of claim 7 wherein each raw strain rate spectrum of said plurality of raw strain rate spectrums is generated from a unique subset of said plurality of complex Doppler packets, and each complex Doppler packet within said unique subset corresponds to a unique sampled depth along an ultrasound beam generated in a scan plane by said ultrasound system.

9. The apparatus of claim 1 wherein said generating and displaying of said plurality of strain rate spectrums is accomplished in real-time as an integrated function of said ultrasound system.

10. The apparatus of claim 1 wherein said generating and displaying of said plurality of strain rate spectrums is accomplished as a post-processing function, independent of real-time operation of said ultrasound system.

11. The apparatus of claim 1 further comprising a display processor responsive to said plurality of strain rate spectrums to generate a strain rate spectrogram that is displayed to an operator of said ultrasound system on a monitor as a spectral time-line image.

12. The apparatus of claim 1 wherein a display format of a spectral time-line image derived from said plurality of strain rate spectrums comprises strain rate versus time.

13. The apparatus of claim 1 wherein a display format of a spectral time-line image derived from said plurality of strain rate spectrums comprises Doppler frequency difference versus time.

14. A method for generating and displaying a plurality of strain rate spectrums in response to Doppler data generated by an ultrasound system corresponding to a tissue segment within a subject, said method comprising performing strain rate processing in response to said Doppler data to generate said plurality of strain rate spectrums, wherein said strain rate processing comprises:

generating a plurality of raw strain rate spectrums; and
generating said plurality of strain rate spectrums in response to said raw strain rate spectrums.

15. The method of claim 14 wherein said generating a plurality of raw strain rate spectrums comprises performing circular convolution processing in response to said Doppler data to generate said plurality of raw strain rate spectrums, wherein said Doppler data comprises two sets of Doppler spectrums; and wherein said generating said plurality of strain rate spectrums in response to said raw strain rate spectrums comprises performing intensity value scaling in response to said plurality of raw strain rate spectrums to generate said plurality of strain rate spectrums, wherein said plurality of strain rate spectrums comprises scaled magnitude values.

16. The method of claim 15 wherein said two sets of Doppler spectrums comprise a first set of Doppler spectrums corresponding to a first sampled depth along an ultrasound beam generated by said ultrasound system and a second set of Doppler spectrums corresponding to a second sampled depth along said ultrasound beam.

17. The method of claim 14 wherein said generating a plurality of raw strain rate spectrums comprises performing spectral estimation processing in response to said Doppler data to generate said plurality of raw strain rate spectrums, wherein said Doppler data comprises two sets of complex Doppler packets; and wherein said generating said plurality of strain rate spectrums in response to said raw strain rate spectrums comprises performing magnitude value scaling in response to said plurality of raw strain rate spectrums to generate said plurality of strain rate spectrums, wherein said plurality of strain rate spectrums comprises scaled magnitude values.

18. The method of claim 15 wherein said two sets of complex Doppler packets comprise a first set of complex Doppler packets corresponding to a first sampled depth along an ultrasound beam generated by said ultrasound system and a second set of complex Doppler packets corresponding to a second sampled depth along said ultrasound beam.

19. The method of claim 18 wherein performing said spectral estimation processing in response to the complex conjugate of a first complex Doppler packet from said first set of complex Doppler packets and a second complex Doppler packet from said second set of complex Doppler packets results in a single raw strain rate spectrum of said plurality of raw strain rate spectrums.

20. The method of claim 14 wherein said strain rate processing comprises: performing complex autocorrelation processing in response to said Doppler data to generate a plurality of complex autocorrelation packets, said Doppler data comprising a plurality of complex Doppler packets; wherein said generating a plurality of raw strain rate spectrums comprises performing spectral estimation processing in response to said plurality of complex autocorrelation packets to generate said plurality of raw strain rate spectrums; and wherein said generating said plurality of strain rate spectrums in response to said raw strain rate spectrums comprises performing magnitude value scaling in response to said plurality of raw strain rate spectrums to generate said plurality of strain rate spectrums, said plurality of strain rate spectrums comprising scaled magnitude values.

21. The method of claim 20 wherein each raw strain rate spectrum of said plurality of raw strain rate spectrums is generated from a unique subset of said plurality of complex Doppler packets, and each complex Doppler packet within said unique subset corresponds to a unique sampled depth along an ultrasound beam generated in a scan plane by said ultrasound system.

22. The method of claim 14 wherein said generating and displaying of said plurality of strain rate spectrums is accomplished in real-time as an integrated function of said ultrasound system.

23. The method of claim 14 wherein said generating and displaying of said plurality of strain rate spectrums is accomplished as a post-processing function, independent of real-time operation of said ultrasound system.

24. The method of claim 14 further comprising performing display processing in response to said plurality of strain rate spectrums to generate a strain rate spectrogram that is displayed to an operator of said ultrasound system as a spectral time-line image.

25. The method of claim 14 wherein a display format of a spectral time-line image derived from said plurality of strain rate spectrums comprises strain rate versus time.

26. The method of claim 14 wherein a display format of a spectral time-line image derived from said plurality of strain rate spectrums comprises Doppler frequency difference versus time.

27. A diagnostic ultrasound scanner for generating and displaying a plurality of strain rate spectrums corresponding to a tissue segment of a subject, said diagnostic ultrasound scanner comprising:
   a front-end transmitting ultrasound energy into said subject along a scan line, said front-end being responsive to said transmitted ultrasound energy backscattered from said subject and generating received beamformed data along said scan line;
   a demodulation module responsive to said received beamformed data and generating complex Doppler packets;
   a Doppler processing module responsive to said complex Doppler packets and generating Doppler spectral data;
   a strain rate processing module responsive to Doppler data and generating a plurality of strain rate spectrums;
   a spectrum buffer module responsive to said plurality of strain rate spectrums and generating a strain rate spectrogram; and
   a display architecture responsive to said strain rate spectrogram and generating a spectral strain rate image.

28. The diagnostic ultrasound scanner of claim 27 wherein said Doppler data comprises said Doppler spectral data.

29. The diagnostic ultrasound scanner of claim 27 wherein said Doppler data comprises said complex Doppler packets.

30. The diagnostic ultrasound scanner of claim 27 wherein a display format of a spectral time-line image derived from said plurality of strain rate spectrums comprises strain rate versus time.

31. The diagnostic ultrasound scanner of claim 27 wherein a display format of a spectral time-line image derived from said plurality of strain rate spectrums comprises Doppler frequency difference versus time.

* * * * *